United States Patent [19]
Falcon et al.

[11] Patent Number: 5,040,978
[45] Date of Patent: Aug. 20, 1991

[54] DENTAL PROPHY ANGLE

[75] Inventors: Charles J. Falcon, Rescue; William C. Foster, El Dorado Hills; Robert L. Walton, Carmichael, all of Calif.

[73] Assignee: Dentsply Research & Development Corp., Milford, Del.

[21] Appl. No.: 456,025

[22] Filed: Dec. 22, 1989

[51] Int. Cl.⁵ .............................. A61C 3/06
[52] U.S. Cl. ............................ 433/125; 433/114; 433/126
[58] Field of Search ............... 433/114, 125, 126, 127, 433/112

[56] References Cited

U.S. PATENT DOCUMENTS

| | | | |
|---|---|---|---|
| 1,688,136 | 10/1928 | Chayes et al. | 433/126 |
| 1,740,796 | 12/1929 | Terry | 433/125 |
| 1,753,352 | 4/1930 | Stark | 433/126 |
| 1,982,336 | 12/1932 | Wiseman | 433/126 |
| 2,300,828 | 2/1940 | Goldenberg | 433/166 |
| 2,315,016 | 2/1941 | Shotton | 433/133 |
| 2,328,270 | 6/1942 | Greenberg | 74/56 |
| 2,469,261 | 5/1947 | Cooper | 433/112 |
| 3,163,934 | 9/1962 | Wiseman | 433/115 |
| 3,478,433 | 4/1968 | Richmond | 433/134 |
| 3,727,313 | 4/1973 | Graham | 433/125 |
| 3,740,853 | 6/1973 | Brahler | 433/112 |
| 3,769,707 | 11/1973 | Condon | 433/126 |
| 3,798,777 | 3/1974 | Reiter | 433/125 |
| 3,869,877 | 3/1975 | Brahler | 433/112 |
| 4,182,041 | 1/1980 | Girard | 433/115 |
| 4,253,832 | 3/1981 | Bailey | 433/115 |
| 4,365,956 | 12/1982 | Bailey | 433/115 |
| 4,486,175 | 12/1984 | Fisher et al. | 433/104 |
| 4,604,058 | 8/1986 | Fisher et al. | 433/127 |
| 4,842,516 | 6/1989 | Choisser | 433/132 |

FOREIGN PATENT DOCUMENTS

| | | |
|---|---|---|
| 928996 | 6/1973 | Canada . |
| 995937 | 8/1976 | Canada . |
| 1060685 | 8/1979 | Canada . |
| 1097957 | 3/1981 | Canada . |
| 1149648 | 7/1983 | Canada . |
| 1171308 | 7/1984 | Canada . |
| 1253016 | 4/1989 | Canada . |
| 1255519 | 6/1989 | Canada . |
| 2498445 | 7/1982 | France . |
| 416935 | 7/1966 | Switzerland . |
| 2011305 | 7/1979 | United Kingdom . |
| 2137503 | 10/1984 | United Kingdom . |

Primary Examiner—Gene Mancene
Assistant Examiner—Michael Lynch
Attorney, Agent, or Firm—Edward J. Hanson, Jr.

[57] ABSTRACT

A prophy angle having a single snap-in retention mechanism that is integral with the housing for retaining the prophy cup rotating member in permanent field position and providing good smooth rotation performance and a detent drive shaft snap-in retention mechanism that locks in position when the dental handpiece is connected.

5 Claims, 2 Drawing Sheets

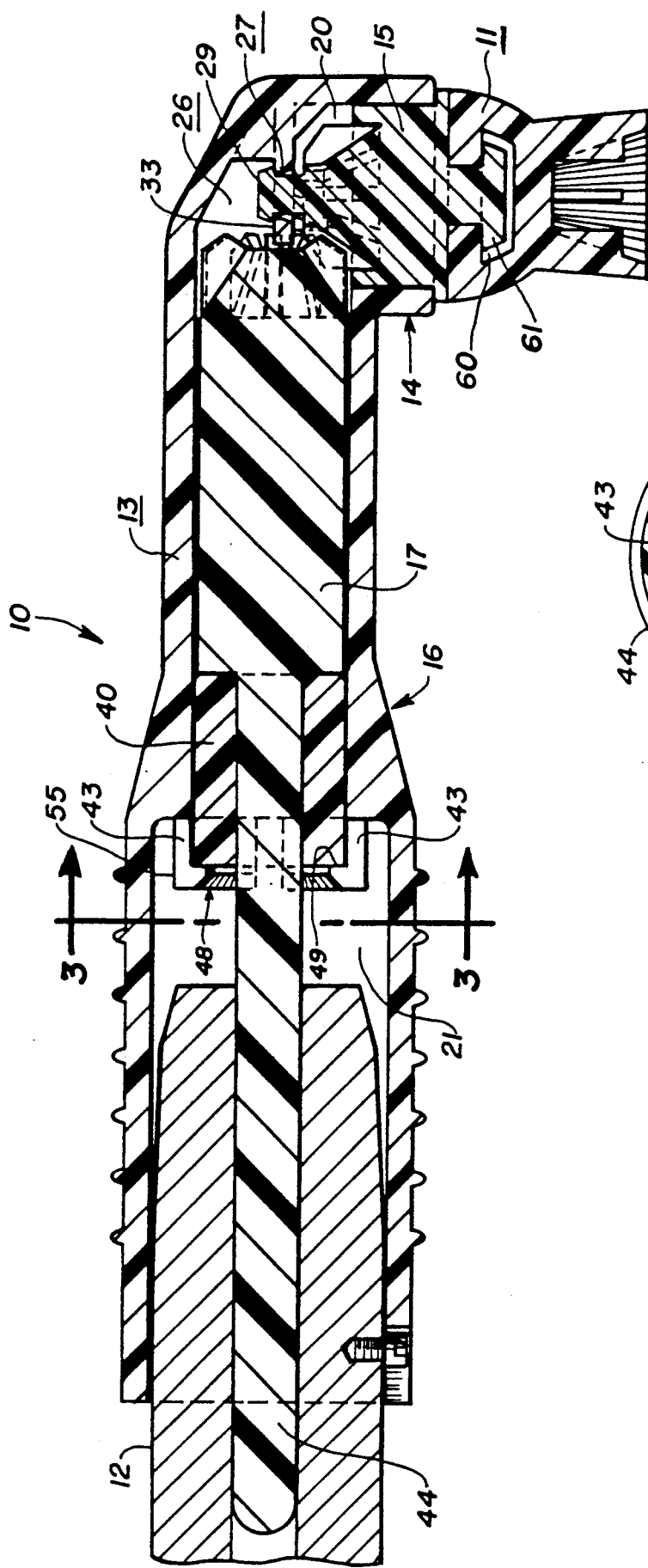
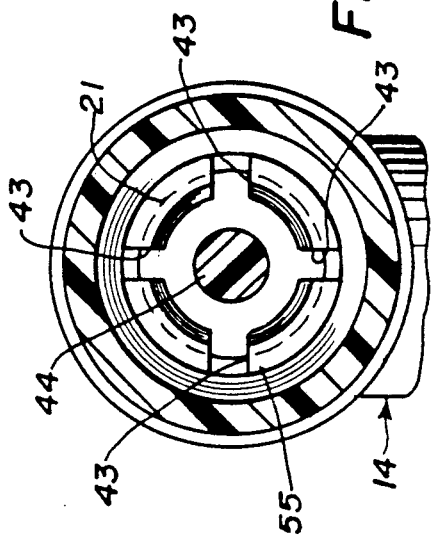
Fig. 1
Fig. 3

5,040,978

DENTAL PROPHY ANGLE

BACKGROUND OF THE INVENTION

This invention relates to dental prophylaxis angles and more especially to those to be thrown away after each patient to avoid cross infection.

There are in the market several disposable prophy angles, dental prophylaxis angles, that are believed to be represented by the disclosures of U.S. Pat. Nos. 3,727,313 and 3,740,853. It is recognized that making reasonably inexpensive but reasonably reliable prophy angles enables the dental professional, dentist or hygienist, to use a prophy angle for a complete prophy of one patient and then discard the prophy angle rather than sterilizing the angle. Sterilization is not only expensive in time and equipment but means handling the contaminated prophy angle.

To reduce cost prophy angles have been constructed of plastic. Plastic has not provided the rugged construction and reliability of steel, but with innovative construction techniques usable inexpensive angles have been provided.

It is an object of the present invention to provide improved disposable prophy angles.

It is a further object to provide prophy angles that can be manufactured less expensively.

It is a yet further object of the present invention to provide prophy angles that give greater reliability in performance.

It is another object of the present invention to provide prophy angles that give smooth, even and consistant performance not only during a prophy treatment of a patient but from one prophy angle to the next so dental professionals will have the same "feel" from one prophy angle to the next prophy angle as they treat a series of patients.

SUMMARY OF THE INVENTION

By an aspect of the invention a prophy cup rotating member is mounted in the prophy angle housing by "snaping" the stud on its inwardly most directed portion through a snap receiving hole integral with the housing and located in the upper portion of the housing passageway receiving the prophy cup rotating member. This provides the sole means for retaining the prophy cup rotating member from falling out of the passageway. The gearing arrangement is such that it tends to eject the prophy cup rotating member from the housing because the gear on the drive shaft engages the prophy cup rotating member driven gear from above. Thus, the reliability of the securement means for the prophy cup rotating member is an important aspect of the present invention.

An aspect of the invention is the permanency of the securement of the prophy cup rotating member in position by shaping the snap stud and the snap receiver such that once the snap connection is made it is permanent. The shape of the matched interface of the snap stud and snap receiver is such that significant damage would have to be done to the interfaces if the snap stud is extracted from its snap secured position of operation. This is obviously of some advantage to patient safety, preventing the prophy cup rotating member from becoming dislodged in a patient's mouth during a prophy treatment.

A further aspect of the invention is the snap engagement of the lock sleeve with the interrupted collar retainer to permanently position the drive shaft in the other passageway of the prophy angle. Again a resilient snap action is provided.

DESCRIPTION OF THE DRAWINGS

FIG. 1 is a substantially central longitudinal sectional view through a prophy angle of the present invention.

FIG. 3 is a cross-section view taken at line 3—3 of FIG. 1.

DESCRIPTION OF THE PREFERRED EMBODIMENTS

Figure 2:
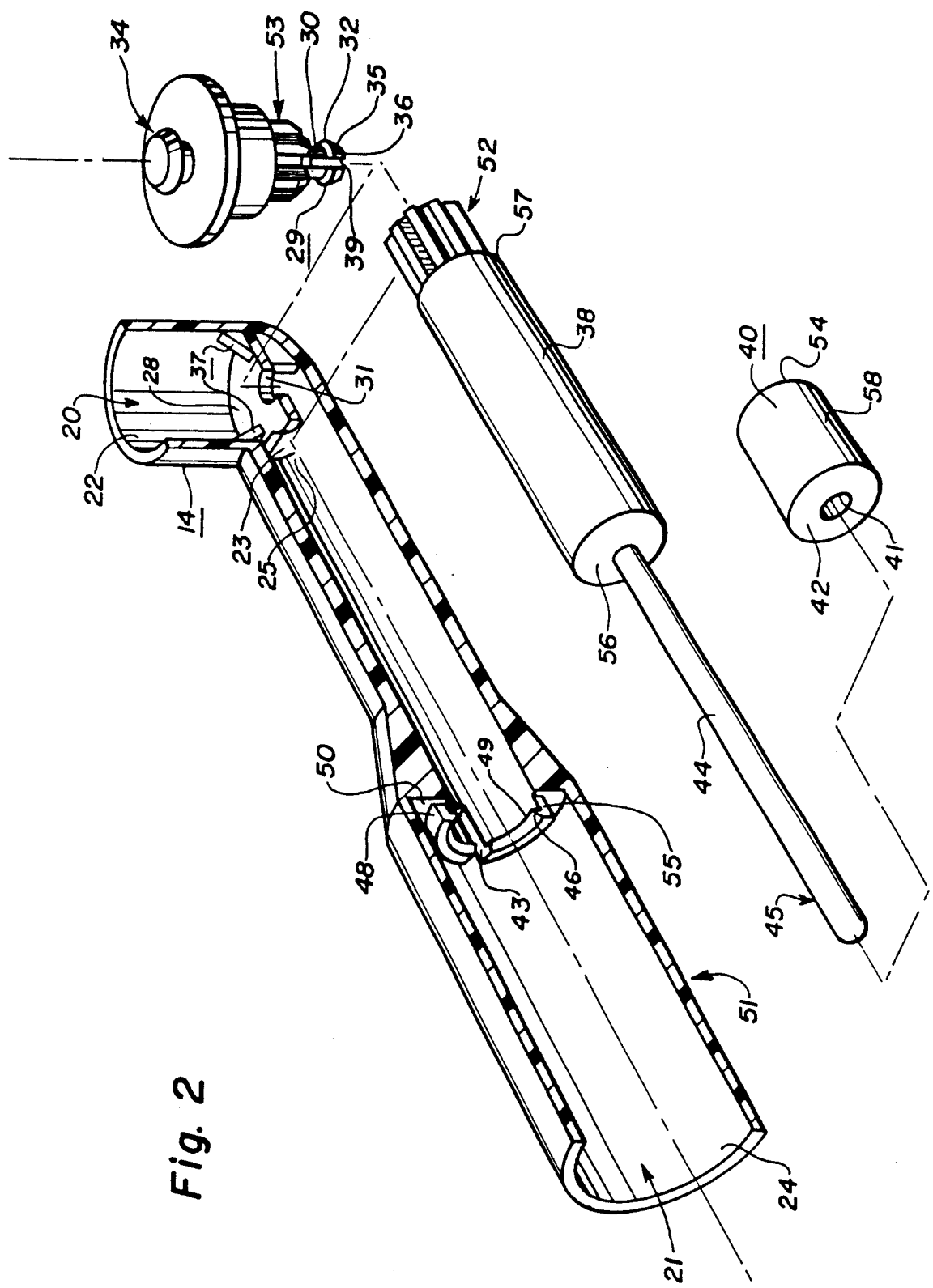
FIG. 2 is an exploded perspective view of the prophy angle of FIG. 1.

Referring first to FIG. 1 of the drawings, a prophy angle, dental prophylaxis right angle, 10 is shown. A prophy cup 11 of a conventional type is shown removably positioned on the prophy angle 10. The nose 12 of a powered dental handpiece of conventional type is also shown.

A housing, 13 is preferably molded as a single integral unitary unit from plastic. By integral unitary, it is meant that the housing is not an assembly of parts welded together or otherwise interconnected, but a single continuous piece of plastic manufactured as a unitary molded part. The gross housing 13 provides a housing 14 for a prophy cup mounting or rotation member 15 and a housing 16 for an elongated drive shaft 17. The housing 14 has a passageway 20 with a central axis that intersects the central axis of a passageway 21 in the housing 16 at an angle. While the intersecting angle is shown as a right angle and a right angle is preferred in most embodiments, in some embodiments other intersect angles may be preferred.

Looking at FIG. 2 it will be understood that housing 14 and its passageway 20 have an outer open end 22 opening out from the gross housing 13 and an inside, inner or inward end with an inner opening 23. The housing 16 and its passageway 21 also has an open end 24 opening out from said gross housing 13 and an inside, inner or inward end with an inner opening 25 which opens into and joins with passage 20. The confluence of passageway 20 and passageway 21 form a mounting and connection section 26 (FIG. 1) of the gross housing 13.

The housing 14, looking at FIG. 1 and FIG. 2, has an attachment retainer 27 that is an integral unitary part of the housing in the form of a strut, shelf 28 (FIG. 2). The prophy cup mounting member or prophylaxis tool mounting member 15 has an end mounting attachment member 29 in the form of a projection or assembly attachment mounting shaft 30 at one end engaged with the attachment retainer 27. In this manner the prophy cup mounting member 15 is attached with and mounted and retained in secured position by the housing 14 in operable position.

Turning now to FIG. 2 it will be seen that the attachment retainer strut 28 is a shelf-like bracket structure that for purposes of expeditious injection molding and function is wholly contained in passageway 20 but is aligned with passageway 21. The shelf 28 extends out from the inside of housing 14 which is part of gross housing 13 in the mounting and connection section 26 of the gross housing 13. The shelf is aligned with the outer opening 24 of the passageway 21 and has a hole or mounting passageway 31 therethrough aligned with the central axis of the second passageway 20. The shelf 28 has a flat retaining surface 33 (FIG. 1) opposite the outer opening 22 of the second passageway and adjacent the hole 31. Webs 37 are strengthening structure.

The prophy cup mounting member projection 30 has a boss or flange 32 at its inner end remote from the prophy cup attachment area or prophylaxis tool mounting portion 34 oriented toward the inside of passageway 20 and sized larger than the hole 31 to be forcibly pushed through the hole 31. The projection 30 preferably has a hollow core at least at its outermost end and has a beveled camming surface 35 therearound to aid in distorting or collapsing the boss inwardly into the hollow core to aid passage of the boss through the hole 31. The hole 31 also has a 15° chamber to aid the flange 32 in passing therethrough. There is a slot 39 in the outer end of the hollow core 30 that passes through the wall around the core at two opposed positions to aid the core in bending or distorting inwardly to allow the flange 32 to pass through the hole 31 without damage to the parts.

The flange 32 has at least one mating retaining surface 36 that is not tapered toward the hole 31. Therefore, after the flange 32 is inserted through the hole 31 the prophy cup mounting member 15 is permanently retained against withdrawal, with the retaining surface 33 on the shelf 28 in mating engagement with the retaining surface 36 on the flange 32. The hole 31 and flat surface 33 serve as an attachment bearing, journaling the attachment shaft 30 remote from the driven gear 53. Preferable the sole means for retaining the prophy cup mounting member 15 within the open end 22 of the housing 14 is the enlarged portion, flange 32 on the attachment shaft 30 engagement with surface 33 on shelf 28.

Turning next to a consideration of the details of mounting the elongated drive shaft 17 in the passageway 21 attention is drawn to both FIG. 1 and FIG. 2. The elongated drive shaft 17 has an enlarged cylinder portion or elongated hub 38, a smaller shaft 44 that is the driving means connection end 45 of the elongated drive shaft 17 and a driving gear portion 52. A locking sleeve 40 fits over the smaller connection shaft 44, preferable the bore 41 of the sleeve 40 is enough larger than the shaft 44 to prevent frictional engagement during operation from the driving means connection end of smaller shaft 44.

Housing 16 has an interrupted collar retainer portion 48 that mates with a locking face 42 of sleeve 40. The interrupted collar retainer or connector 48 is preferably segmented by slots 43 into a plurality of arms 55 with hook or catch ends 46 having flat faces 49 that snap on to registration with face 42 of sleeve 40 when the cam surfaces 50 are pushed out by the bearing face 54 of the sleeve 40. The control of the resiliency of the snap engagement is provided by the length and thickness of the arms which corresponds to the depth of the slots 43. There are preferably 4 arms and corresponding slots although this can be varied in proper instances and could be desirable from 2 to 6 or even 8 or more in some situations.

The drive shaft 17 has a bearing face 56 which bears against and is frictionally engaged with bearing face 42 of the locking sleeve 40. The only other observed bearing or frictional rotational engagement observed for the drive shaft is in the area 57 where it has been observed the drive shaft leaves a rubbed area on the inside of housing 14 when the parts have been assembled and tested for operation of prototypes. This construction has been found not to develop excess heat during operation.

Turning next to consideration of the provision of the driving connection between the driving gear 52 on the elongated drive shaft 17 and the driven gear 53 of the prophy cup rotating member 15, attention is again directed to both FIG. 1 and FIG. 2. The driving gear 52 is remote from the driving means, dental handpiece, connection end of the elongated drive shaft 17. The driven gear 53 is intermediate the end mounting attachment member 30 and the cup attaching area 34 of the prophy cup rotating member 15. The driving gear 52 and the driven gear 53 mesh in the mounting and connection section of the gross housing 13 as shown in FIG. 1 with the driving gear 52 accessing the housing 14 from its side and from the housing 16 through the opening 25. This provides a driving connection of the driving gear 52 and the driven gear 53.

Turning next to the engagement of the prophy cup 11 on prophy cup rotation member 15, attention is again directed to both FIG. 1 and FIG. 2. The device shown for engaging the prophy cup tool on the prophylaxis tool mounting portion 34 of the prophy cup rotation member 15 is a snap over pocket 60 in the resilient "rubber" prophy cup 11 and a stud 61 with an enlarged head. The pocket is sized to match the stud for a tight fit securing the cup tightly against the exposed part of the prophylaxis tool mounting portion 34 in conventional manner. The prophylaxis cup may be of various configurations and a number of configurations are available in the market. The snap arrangement for attaching the prophy cup is also known in other configurations and is not a part of the present invention. It is also known to tap the tool mounting area of the prophylaxis tool mounting member with screw threads for a threaded mounting of the prophy cup in conventional manner. Another preferred embodiment of the prophy cup mounting arrangement involves forming a small cylindrical extention on the stud 61 and a corresponding cylindrical cavity at the bottom of pocket 60 to further stabilize the prophy cup. If the cylindrical cavity is slightly deeper than the portion engaged by the extension on the stud then even more of the material from which the prophy cup is made may be saved.

Turning next to the cross-sectional view taken at line 3—3 of FIG. 1, the locking sleeve can be seen engaged on the small shaft 44 of the long gear with the arms 55 of the collar locked onto face 42 (FIG. 2). The slots 43 separate the arms 55. The passage 21 within which the shaft 55 is held by the bushing locking sleeve 40 (FIG. 2) is also designated.

Turning now to the engagement of the dental handpiece 12 which powers the prophy angle with the prophy angle, attention is called to FIG. 1. The passageway and the driving means connection end of the drive shaft will accept a variety of dental handpieces, although only one type is shown for purposes of illustration. The smaller shaft 44 of the drive shaft 17 is engaged by a dental handpiece in conventional manner well known in the dental profession.

In the course of manufacturing the housing 13, the drive shaft 17, and the driven member 15 will be injection molded with the housing being formed of polyester (Celanex 2000 product Hoechst Celanese Corp.) and the drive shaft and driven member from Nylon 66-plus mineral filler and short glass fibers (Minlon 22C a product of Dupont). The locking sleeve 40 is preferably constructed of a material suitable as an excellent bearing member such as nylon to aid to low friction rotation.

The material used was Nylon (Zytel 101-L a product of Dupont).

It has been found advantageous with a stud height of 0.121 inch and hollow core wall thickness of 0.035 inch in the present construction of the driven member to provide a slot depth of 0.121 inch and a flange thickness in height of 0.068 inch and width of 0.0365 inch. The gear teeth on the short gear are on a hub diameter of 0.2730 with the gears being straight bevel involute 32 DP. There are 7 teeth on each gear. The pitch angle is 20° and the pitch diameter is 0.21875 inch. The preferred pitch diameter would be pitch 0.185 to 0.2315 inch. The pitch angle is preferably 10° to 30°, more preferably 15° to 25°. The arms 55 for locking the locking sleeve in position have been advantageously made 0.163 inch long and 0.163 wide and 0.0190 thick in its thinnest section. The hub at area 57 has a diameter of 0.2235 inch. The long gear has a diameter of 0.2215 inch on the gear hub. The gears on the long gear are identical to those on the short gear with an interference of 0.055 inch between the gears. The preferred gear interference is 0.025–0.1 more preferably 0.040 to 0.07 inch. Good gear mesh is provided by the size of gear teeth and their design or shape. This helps in preventing striping of the gears or disconnection of the gears.

To form the gears it was found that a Gleason gear cutting machine was an expeditious machine for machining the gear teeth in the blank used in making the injection mold for the long and the short gear. The gear teeth have a working depth of 0.055 inch allowing a pull-back of up to 0.020 in the position of the long gear in the housing without materially diminishing working mesh of the gears which would remain 0.035 inch. When the handpiece connects with the right angle it tends to pull or push the long gears position within the housing and this allows good operation.

To mold the housing 13 it will be understood that it is very much preferred to have the attachment retainer housing part 27 in line with both passage 21 and passage 20 to enable the withdrawal of the core pins. It is also preferable to have a small hole in the housing opposite the end mounting member 29 to secure the core pin in position and reduce flash.

After the parts have been molded and cleaned up to remove any flashing and the like the locking sleeve 40 is assembled with the driving shaft 17. The small shaft 44 of the long gear 17 is inserted through the bore 41 of the locking sleeve 40 bringing an end of the locking gear which will thereby become the bearing surface 54 into engagement with the bearing surface 56 on the long gear 17. Then the assembly is snapped into position with the arm 55 of housing 16 engaging the face 41 of the sleeve 40 due to the resiliency of skirts arms 55 which are cammed out by engagement of the camming surfaces 50 engaging with and ride over the outer cylindrical surface 58 of the locking sleeve 40.

The stud that is the shank or projection 15 and boss 30 are inserted into the hole or eyelet 31 with the boss or head 30 being forced through, deforming as it passes through and then extending to permanently mount the driven member 15 within the housing against accidental separation.

Thereafter the driven prophy cup 11 is snapped over stud 61 on the short gear 53 mounting member 15 is snapped into position.

The completed prophy angle is then packaged. Of course, the prophy cups can be supplied separately.

To operate the prophy angle, an angle is positioned on a handpiece as shown in FIG. 1 and the prophy cup is loaded with prophy paste by a dental professional in the dental operatory. Then a dental patient is provided with prophylaxis treatment in the usual manner. Of course the prophy cup is usually refilled with prophy paste from time to time. At the end of a prophylaxis treatment the prophy angle should be disposed of in an environmentally approved manner. It is intended that a prophy angle of this invention only be used on a single patient and then discarded.

It will be obvious to those skilled in the art that various changes and modifications may be made in the invention without departing from its true spirit and scope. It is, therefore, aimed in the appended claims to cover all such equivalent variations as fall within the true spirit and scope of the invention.

What is claimed is:

1. A dental prophylaxis angle comprising:
   (a) an elongated drive shaft, said drive shaft comprising:
      (i) a small shaft portion extending to a driving means connection end,
      (ii) at least one intermediate drive shaft mounting connection comprising at least one locking sleeve having a central bore received on said small shaft portion, and
      (iii) driving gear remote from said driving means connection end;
   (b) prophy cup rotation member, said prophy cup rotation member comprising:
      (i) prophy cup attachment area at one end of said prophy cup rotation member, and
      (ii) end mounting attachment member comprising a projection at the other end of said prophy cup rotation member remote from said prophy cup attachment area and attaching said prophy cup rotation member in operable position,
      (iii) driven gear intermediate said end mounting attachment member and said cup attachment area; and
   (c) housing comprising:
      (i) first passageway opening outwardly for coupling with a driving means and receiving said drive shaft and having at least one locking arm engaging said locking sleeve mounting said drive shaft in said first passageway,
      (ii) second passageway opening outwardly and receiving said prophy cup rotation member, and
      (iii) mounting and connection section at the confluence of said first passageway and said second passageway for mounting the prophy cup rotation member and providing for the driving connection of the driving gear of said elongated drive shaft and said driven gear of said prophy cup rotation member, said mounting and connection section comprising a mounting strut mounting and retaining said prophy cup rotating member in secured position.

2. The dental prophylaxis angle of claim 1 wherein said attachment retainer comprises a shelf extending out from the inside of said housing in said mounting and connection section in alignment with the outer opening of said first passageway and having a hole therethrough aligned with the central axis of said second passageway, said shelf having at least one retaining surface opposite the outer opening of said second passageway and adjacent said hole that is not tapered toward or into said hole, said prophy cup mounting member projection having a boss adjacent its end remote from said prophy cup attachment area sized to be forcibly pushed through said hole in said shelf and having at least one camming surface to aid passage through said hole and at least one mating retaining surface that is not tapered toward said hole after insertion through said hole whereby said prophy cup mounting member is permanently retained against withdrawal when mounted through said hole in said shelf with said at least one retaining surface and said at least one mating retaining surface in mating engagement.

3. The dental prophylaxis angle of claim 2 wherein said first passageway has a driving means receiving portion and wherein said locking sleeve is mounted on said shaft without intermediate structure and provides a bearing surface for said drive shaft at one of its ends but not where said drive shaft passes through said central bore and said drive shaft having an elongated hub that has a face in rotating bearing engagement with said bearing surface of said locking sleeve.

4. A dental prophylaxis angle comprising:
  a prophylaxis tool mounting member, said prophylaxis tool mounting member comprising an assembly attachment shaft, prophylaxis tool mounting portion remote from said assembly attachment shaft and driven gear intermediate said assembly attachment shaft and said prophylaxis tool mounting member:
  a housing having a central axis and mounting said prophylaxis tool mounting member, said housing comprising an open end receiving said prophylaxis tool mounting member and exposing said prophylaxis tool mounting portion, an attachment bearing comprising a shelf extending out from the inside of said housing and having a hole therethrough aligned with said central axis of said housing and journaling said assembly attachment shaft of said prophylaxis tool mounting member within said hole and retaining said assembly attachment shaft with a retaining surface of said shelf opposite said open end and adjacent said hole that is not tapered toward or into said hole and an opening from the side of said housing for access with a driving gear and;
  an enlarged portion on said attachment shaft journaled by said attachment bearing, said enlarged portion of said attachment shaft remote from said driven gear sized to require forcible insertion through said hole in said shelf and having at least one camming surface to aid passage through said hole and at least one mating retaining surface that is not tapered toward said hole after insertion through said hole whereby said prophylaxis tool mounting member is permanently retained against withdrawal when mounted through said hole in said shelf with said retaining surface and said at least one mating retaining surface in mating engagement and being the sole means retaining said prophylaxis tool mounting member within said open end of said housing.

5. The dental prophylaxis angle of claim 4 wherein said enlarged portion of said attachment shaft is at the outer end of said attachment shaft and has a portion of its structure of the enlarged dimension removed allowing said enlarged portion to be collapsed inwardly to aid in insertion of said enlarged portion through said hole in said shelf.

* * * * *